United States Patent
Langer et al.

(10) Patent No.: US 8,071,792 B2
(45) Date of Patent: *Dec. 6, 2011

(54) HIGH-PURITY VINYLENE CARBONATE AND A METHOD OF PURIFYING VINYLENE CARBONATE

(75) Inventors: Reinhard Langer, Tönisvorst (DE); Paul Wagner, Düsseldorf (DE); Heinrich Grzinia, Erkelenz (DE)

(73) Assignee: Saltigo GmbH, Langenfeld (DE)

( * ) Notice: Subject to any disclaimer, the term of this patent is extended or adjusted under 35 U.S.C. 154(b) by 572 days.

This patent is subject to a terminal disclaimer.

(21) Appl. No.: 11/920,041

(22) PCT Filed: May 4, 2006

(86) PCT No.: PCT/EP2006/004153
§ 371 (c)(1),
(2), (4) Date: Jan. 13, 2009

(87) PCT Pub. No.: WO2006/119907
PCT Pub. Date: Nov. 16, 2006

(65) Prior Publication Data
US 2009/0216038 A1      Aug. 27, 2009

(30) Foreign Application Priority Data
May 12, 2005   (DE) .......................... 10 2005 021 967

(51) Int. Cl.
*C07D 317/40*      (2006.01)
(52) U.S. Cl. ...................................... 549/230
(58) Field of Classification Search .................... 549/230
See application file for complete search history.

(56) References Cited

U.S. PATENT DOCUMENTS 2,873,230 A   2/1959   Thomas et al. ................. 202/66
6,395,908 B1  5/2002   Seifert et al. ................... 549/229

FOREIGN PATENT DOCUMENTS

| | | |
|---|---|---|
| DE | A 1 135 452 | 8/1962 |
| GB | A 899 205 | 6/1962 |
| JP | 2000-026449 | 1/2000 |
| JP | 2002-226475 | 8/2002 |
| JP | 2002-322171 | 11/2002 |
| JP | 2002-346303 | 12/2002 |

OTHER PUBLICATIONS

Newman, M. and Addor, R.; JACS, 1953, p. 1263.
Newman, M. and Addor, R.; JACS, 1955, p. 3789.
Johnson, W.K., et al.; JOC, (1960) p. 1042.
Huang et. al.; Chinese Journal of Polymer Science, (1990) vol. 8, No. 3, pp. 197-203.
Zief, M., et al.; Journal of Chemical Education (1963) vol. 40, pp. 351-352.

*Primary Examiner* — Bernard Dentz
(74) *Attorney, Agent, or Firm* — Michael A. Miller

(57) ABSTRACT

The present invention relates to the technical purification of vinylene carbonate (VC) by means of a simple thermal treatment with organic compounds which possess amidic nitrogen-hydrogen bonds, followed by a distillation and a melt crystallization. In this way VC of ultra-high purity is obtained. The high-purity vinylene carbonate can be stored and transported without stabilizer.

4 Claims, No Drawings

HIGH-PURITY VINYLENE CARBONATE AND A METHOD OF PURIFYING VINYLENE CARBONATE

The present invention relates to high purity vinylene carbonate (VC) in the solid state of aggregation and to a process for the purification of vinylene carbonate. Vinylene carbonate is an important intermediate for the production of chemicals, pharmaceutical products, crop protection agents and in particular for polymers, coatings and battery electrolytes.

Vinylene carbonate is produced by a known method by eliminating hydrogen chloride from chloroethylene glycol carbonate by means of tertiary amines, in particular triethylamine.

Chloroethylene glycol carbonate is obtained by free radical chlorination of ethylene glycol carbonate by means of chlorine or sulphuryl chloride.

This synthesis was published for the first time in 1953 by Newman und Addor (JACS, 1953, page 1263; JACS 1955, page 3789).

Ethylene glycol carbonate (GC) was photochlorinated as such by means of ultraviolet light at 60-70° C., and the resulting CGC was purified by vacuum distillation.

Newman and Addor obtained VC by elimination by means of triethylamine in boiling ether, the mixture having been heated overnight.

The isolation was effected by filtering off the triethylammonium chloride and then carrying out distillation, which gave a crude VC in a yield of 59%, which crude VC had to be purified by further distillation.

JP 2000/026449 describes the elimination in high-boiling solvents (b.p. 170-300° C.). The reaction is explicitly effected with triethylamine in dibutyl carbonate for 20 hours at 50° C. After the ammonium chloride has been filtered off and excess triethylamine distilled off, crude VC is isolated by simple distillation. In order to remove traces of amines, the VC is poured over a silica gel column. Finally, purifying distillation is carried out. The chlorine content of the VC thus obtained is stated at 29 ppm, whereas comparative samples contain >3000 ppm. The yield was 56%.

DE-A 19 955 944 claims the elimination in GC as a solvent (b.p. 243-244° C.). CGC is initially introduced in GC and reacted in 1.5 hours by addition of triethylamine at 60° C. After excess triethylamine has been distilled off at 40° C. and evaporation has been effected via a thin-film evaporator at 100° C., a colorless mixture of VC and GC is obtained in a yield of 73%. No data are given concerning the purity.

After the salts have been filtered off and the solvent and other impurities have been separated by simple distillation, the reactions of CGC in the liquid phase give a crude vinylene carbonate which is contaminated with residues of chloroacetaldehyde, chloroglycol carbonate, dichloroglycol carbonate and further organic compounds, some of which contain chlorine.

Johnson and Patton describe, in JOC, 1960, page 1042, the reaction of CGC over fixed beds of $CaSO_4$ catalysts in the gas phase at 250° C. and 50-60 mmHg.

The catalysts undergo very rapid deactivation and at best achieve a conversion of 35-40% at a selectivity of 40-45%. Higher or lower temperatures lead to a lower conversion. The catalysts can be regenerated by burning off.

Granulated active carbon and granulated activated alumina give only gaseous products.

DE-A 1 135 452 describes the HCl elimination of CGC at 300-400° C. The CGC is passed in gaseous form over an inert support material which is coated with elements of subgroup I, II or VIII of the Periodic Table of the Elements or salts or oxides thereof. Preferably, the chlorides of iron, of cobalt, and of copper, particularly preferably cadmium chloride, are used. Suitable support materials are pumices and silicates having particle sizes of 4 to 8 mm.

The catalysts are operated as a stationary bed at atmospheric pressure or reduced pressure and a temperature of 270 to 450° C., preferably of 300-400° C.

The behavior of $CdCl_2$ on pumice is explicitly described. The catalyst has a substantially longer on-stream time (about 270 hours) and higher selectivity (74%) than the $CaSO_4$ catalysts.

The space velocity was 0.15 kg of CGC per l of catalyst per hour and the inert gas stream was between 27 and 67 l per kg of CGC. The average conversion was 87%.

The catalyst can be burnt off at 500 to 700° C. with air.

The gas-phase process for the production of vinylene carbonate gives, after a simple distillation, a crude vinylene carbonate which is very similar to the liquid processes with regard to impurities.

Regarding the effort for purification by distillation, the data in the literature are inexact, so that it is not possible to estimate the effort expended in the specific case and the losses of yield due to the purification.

A high purity of the VC is of great technical importance particularly for the applications of polymerization and as an additive for battery electrolytes.

U.S. Pat. No. 2,873,230 states that, even with an 80-tray column, VC produced by the method of Newman and Addor cannot be sufficiently purified in order to be copolymerized with vinyl acetate, and insufficient molecular weights are achieved in the homopolymerization.

Chlorine-containing impurities are said to be responsible for this. The application relates to a purification method which consists in vaporizing the VC subjected to a purifying distillation and feeding it in gaseous form to thermal treatment at 200 to 450° C. The VC thus obtained is again subjected to purifying distillation, and only thereafter is a purity for satisfactory polymerization results achieved.

Huang et. al., in Chin. J. Polm. Sci. (1990) 8 (3), 197-203, state that VC produced by the method of Newman and Addor, after it has been isolated by filtration and the solvent distilled off, is stirred for 1 hour with about 4% of NaBH4 at 64° C. and only thereafter subjected to a purifying distillation. This procedure must be repeated in order to obtain readily polymerizable material which is stable to discoloration.

Neither of the two literature references discusses in detail the content of impurities which has remained in the pure VC. Losses due to the isolation procedure are likewise not discussed.

GB-A 899 205 describes the purification by repeated melt crystallization of VC prepared according to Newman and Addor. In order to obtain polymers having a high molecular weight, it is necessary to use VC having a melting point greater than 21° C. that is obtained by crystallization four times. Here too, the purity of the VC is not discussed directly and just as little is said about the disposition of the mother liquors. Since the VC has been prepared as described in JACS 75, 1263 (1953), distilled VC was used in the crystallization.

In Journal of Chemical Education (1963, Vol. 40, pages 351-2), Zief and Ruch describe the purification of VC by zone melting. A monomer having a melting point of 22° C. and a chlorine content of 1-1.8% reaches a chlorine content of 500 ppm after zone melting once; after a further 3 passes through the zone melting apparatus, the VC reached a chlorine content of 50 ppm. The more contaminated the VC, the more zone melting runs the material requires, and then upstream distillation therefore occurs as expedient to the authors.

JP 2002-322171 describes the combination of distillation and crystallization for purifying VC. For the crystallization, solvent mixtures comprising an aromatic component and an aliphatic hydrocarbon are claimed. The yield by distillation and crystallization in the examples is 60 and 83%. The purity is above 99.95%. Ethylene glycol carbonate impurities of 400 and 25 ppm and chloride contents of 15 ppm remain in the VC.

JP 2002-346303 describes the crystallization of VC from solutions with minimization of the crystals adhering to the vessel wall. Mixtures of toluene and hexane are used as solvents. Purities of 99.8% to 99.93% with yields of 14% to 81% are described.

JP 2002-226475 describes the crystallization of VC from solvent mixtures which are formed from a polar solvent and/or an aromatic component and an aliphatic hydrocarbon. Toluene-hexane mixtures are once again mentioned in the examples. With a yield of 93.2%, a 99.94% pure VC which contains 11 ppm of chloride is obtained.

In the applications which relate to purification by crystallization, either particularly large amounts of solvents are employed or the crystallization process has to be repeated several times in order to achieve high purities.

When solvents are employed, the VC must finally be distilled again if it is intended to remove considerable residuals of solvent from the VC.

It should be noted that the methods of analysis for determining the purity are not described in detail in the literature, so that the purity data are not unambiguous.

Stabilizer-free pure VC tends to polymerize and is therefore made available commercially with stabilizers such as BHT (Butylhydroxytoulene). The purer the monomer, the more sensitive it is to unintended polymer formation.

It is an object of the invention to provide high-purity vinylene carbonate and to develop a process for the purification of vinylene carbonate.

Surprisingly, it was found that a high degree of purity of VC is achieved if, before the purifying distillation, a simple thermal treatment with organic compounds which have amidic nitrogen-hydrogen bonds is carried out. This is possible regardless of whether the industrial VC was obtained by elimination in the liquid phase or in the gas phase. If this VC is subjected to a melt crystallization, VC of the highest purity is obtained; the resulting mother liquor is recycled into the upstream purification steps, thus incurring only minimal losses of VC.

The invention therefore relates to high-purity VC, characterized in that the VC has a stabilizer content of less than 100 ppm, preferably less than 10 ppm, and is particularly preferably stabilizer-free and has a content of 99.9 to 99.99999%, preferably 99.99 to 99.9999%, and is present in the solid state of aggregation.

The invention further relates to a process for the purification of vinylene carbonate, in which the vinylene carbonate to be purified
  a) at a temperature in the range of 25 to 180° C. is contacted with an organic compound having at least one amidic nitrogen-hydrogen bond,
  b) if appropriate any precipitated solid is filtered off,
  c) the vinylene carbonate purified in this way is distilled via a column and
  d) the purified vinyl carbonate is obtained from the distillate by crystallization.

In the context of the invention, organic compounds having amidic nitrogen-hydrogen bonds are all aliphatic and aromatic carboxamides which have one or more of the following functional groups of the following formula (I)

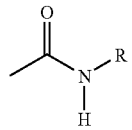

in which R=H, $C_1$-$C_{10}$-alkyl or cycloalkyl, $C_6$-$C_{10}$-aryl, or ureas of the following formula (II)

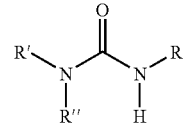

in which R, R' and R'' are identical or different and are H, $C_1$-$C_{10}$-alkyl or cycloalkyl, $C_6$-$C_{10}$-aryl, ureas preferably being used.

Organic compounds having amidic nitrogen-hydrogen bonds from the group consisting of formamide, methylformamide, acetamide, methylacetamide, ethylacetamide, phenylacetamide, adipamide, benzamide, phthalamide and propionamide are preferably used. Dimethylurea, diethylurea and diphenylurea are particularly preferably used. Urea is very particularly preferred.

The thermal treatment in step a) is effected with stirring at temperatures between 25 and 180° C., preferably between 60 and 160° C., particularly preferably between 90 and 140° C.

Relative to the vinylene carbonate, 0.1-30% by weight, preferably 1-10% by weight, particularly preferably 2-6% by weight, of purification substance are added.

The addition of the organic compound having at least one amidic nitrogen compound can be effected in the presence of or without addition of solvents. For example, dimethylacetamide, N-methylpyrrolidone, dimethylformamide and DMSO may be mentioned as solvents.

After the thermal treatment, the vinylene carbonate is distilled off from the residue in step c). This can be carried out as a batch distillation from a container via a column having at least 10, preferably at least 20, particularly preferably at least 30, trays.

Suitable column internals are all possibilities known to the person skilled in the art, for example bubble trays, sieve trays and furthermore random packing, such as, for example, Raschig rings, Pall rings, Berl saddles, and also cross-channel structures, such as, for example the structured packings from Sulzer and Montz.

The low boiler-rich first runnings of the purifying distillation which are obtained by the process according to the invention are advantageously collected and distilled separately for discharge of these low boilers with little loss, the VC thus obtained again being recycled to the thermal treatment in step a) and/or purifying distillation in step b).

The VC obtained is subjected to a melt crystallization in the process according to the invention in step a) with a content between 99.0 and 99.99, preferably between 99.5 and 99.9%.

The melt crystallization can be carried out in industrial plants of the kind known to the person skilled in the art; tube-bundle crystallizers may be mentioned in particular.

After the isolation, the VC is obtained in very high purity, with residual chloride contents of <10 ppm.

The mother liquor obtained in the crystallization can be recycled, preferably including the melt liquid, directly to the distillation in step c) and/or thermal treatment in step a).

Surprisingly, it was found that stabilizer-free VC in the solid state can be stored unchanged over a long time.

Below, the process according to the invention is illustrated with reference to some examples, but the examples are not to be understood as limiting the concept of the invention.

EXAMPLES

Apparatus Used:

The distillation apparatus consisted of an oil-heated 15 l pot having a plane-ground joint and an anchor stirrer, column, reflux splitter, condenser and an apparatus for establishing a constant vacuum. A cold trap cooled to −78° C. was present before the vacuum pump. The pot having a plane-ground joint, column, reflux splitter and condenser were made of glass, and the anchor stirrer of Teflon.

The column had 1500 mm long Sulzer DX structured packing comprising Hastelloy C having a diameter of 50 mm. Structured packings of this type have separation efficiencies of between 15 and 30 trays per meter.

The apparatus was always blanketed with nitrogen before and after loading and before operation.

Example 1

Purification of VC

Crude VC freed substantially only from polymeric impurities by a preliminary distillation without a column was used as starting material.

This crude VC was about 97% pure and had a content of organic and inorganic chlorine of about 0.5% to 1%.

The gas chromatographic analysis was effected by means of an HP 6890. Separation was effected over a 50 meter long CP-Sil 8 CB having an ID of 0.53 mm and an FD of 1.0 µm.

The carrier gas was nitrogen at an admission pressure of 5 psi. The injector was operated with a flow of 138 ml/min and a split of 30/1.1 µl of pure VC was injected.

The injector temperature was 220° C., and the detector temperature 320° C. The temperature program started with 50° C. with heating at 5° C./min to 250° C.

Evaluation was effected according to the standard % method.

1st Process stage: Treatment with Urea At 140° C., Filtered Off with Suction, Diluted with NMP:

200 g of urea were added to 12 060 g of crude VC and the mixture was stirred under nitrogen for 2 hours at 140° C. After cooling to about 30-40° C., 235 g of the solid were filtered off, 11 743 g of liquid were transferred to the distillation apparatus described above and 1000 g of NMP were added.

The mixture was refluxed at a pressure of about 35 mbar and then first runnings were distilled off at a reflux ratio of 30/1.

About 160 g of distillate which, according to GC analysis, comprised 96% of VC were thus obtained in the course of 2.5 hours. In the following 3.5 hours, about 400 g of a distillate which comprised 97.5% of VC were obtained, followed by about 470 g of distillate having a VC content of 99.4%, which distilled over in 2.5 hours.

The main run was then taken off at a reflux ratio of 5/1. About 9600 g of a 99.9% pure VC which had a chlorine content below 50 ppm distilled over in 26 hours.

About 1100 g of bottom product having a VC content of less than 0.5% remained.

The cold trap was virtually empty.

The mass balance was virtually quantitative, 93% of VC was recovered.

84% of the vinylene carbonate were obtained in the main fraction.

2nd Process Stage Crystallization in a Static Crystallizer:

The crystallizer consisted of a 400 mm long thermostatic glass tube having an internal diameter of 30 mm. A perforated disk for fixing the crystals and a discharge valve for the mother liquor were mounted at the lower end. An argon-flushed interchangeable receiver was present below the shut-off valve. At the upper end, the gas phase could be replaced by flushing with argon, and furthermore a coolable plastic finger extended into the interior, by means of which the crystallization could be initiated in the targeted manner.

302 g of the distillate from the 1st process stage were sensed into the crystallizer and the gas phase was displaced by flushing with argon. The vinylene carbonate was cooled down by means of a cold oil circulation at 19° C. Thereafter, the crystallization was started by cooling of the cold finger and allowed to run for 4 hours.

Rapid propagation of a crystal front from the cold finger over the entire heat exchanger surface is observed. The crystals then grew in a strikingly compact manner inwards.

After 4 hours, by opening the valve at the lower end, the first liquid below the perforated plate in the uncooled part of the tube and then the mother liquor were discharged and were collected separately. Thereafter, the receiver was changed again and the oil circulation was heated to 22° C. in 1 h with a linear ramp with the valve open and was kept at 22° C. for a further hour, the crystals being purified by sweating. Finally, the main fraction was melted at 30° C. into a further receiver.

The starting material was about 99.9% pure and had a chlorine content of <50 ppm and a water content of about 100 ppm.

24 g of first runnings were collected, with a VC content of 99.87%, a chlorine content of about 110 ppm and a water content of about 230 ppm.

56 g of mother liquor were obtained, with a VC content of 99.8%, a chlorine content of 160 ppm and a water content of 330 ppm.

The sweat weighed 35 g and had a content of 99.9% of VC, 70 ppm of chlorine and 110 ppm of water.

The product melt weighed 187 g, had a VC content of 99.99%, was at the limit of detection with 3 ppm of chlorine and contained 10 ppm of water.

Mother liquor, first runnings and sweat can be recycled directly to the urea treatment or the distillation and are therefore not lost.

Example 2

Comparison of the Properties of Liquid and Solid VC

Samples of vinylene carbonate, purified according to Example 1, was stored without stabilizer with exclusion of light as a liquid at 20° C. and in crystalline form at 5° C.

Liquid VC:

The stabilizer-free samples of vinylene carbonate showed slight to strong yellow colorations and slight turbidity phenomena after 70 days. The content, measured by ISTD, much to 96%. In the absence of stabilizer, highly pure vinylene carbonate in the liquid state is not storage-stable.

Solid VC:

The samples stored at 5° C. in the solid state were all colorless and clear after melting, even after 365 days. The analyses showed no changes in the quality. Stabilizer-free vinylene carbonate is stable during storage in the solid state.

The invention claimed is:

1. A Process for the purification of vinylene carbonate, comprising
   a) contacting vinylene carbonate to be purified with and organic compound having at least one amidic nitrogen-hydrogen bond at a temperature in the range of 25 to 180° C.,
   b) filtering off any precipitated solid formed in step a),
   c) distilling the result of step b) via a column; and
   d) crystallizing the distillate to obtain purified vinyl carbonate.

2. The process according to claim 1, characterized in that the organic compound having at least one amidic nitrogen-hydrogen bond is added in an amount of 0.1 to 30 by weight, based on vinylene carbonate, to the vinylene carbonate.

3. The process according to claim 1 wherein the organic compound having at least one amidic nitrogen-hydrogen bond comprises urea.

4. The process according to claim 2 wherein the organic compound having at least on amidic nitrogen-hydrogen bond is added in an amount from 1 to 10% by weight, based on vinylene carbonate, to the vinylene carbonate.

* * * * *